US008460224B2

(12) United States Patent
Wilford et al.

(10) Patent No.: US 8,460,224 B2
(45) Date of Patent: Jun. 11, 2013

(54) THERAPEUTIC COMPRESSION APPARATUS

(76) Inventors: Michael L. Wilford, Chicago, IL (US); John Crane, Woodridge, IL (US)

( * ) Notice: Subject to any disclaimer, the term of this patent is extended or adjusted under 35 U.S.C. 154(b) by 500 days.

(21) Appl. No.: 12/798,689

(22) Filed: Apr. 9, 2010

(65) Prior Publication Data

US 2011/0251536 A1 Oct. 13, 2011

(51) Int. Cl.
*A61H 7/00* (2006.01)
*A61H 19/00* (2006.01)
*A61F 5/00* (2006.01)

(52) U.S. Cl.
USPC .......................................... 601/151; 602/23

(58) Field of Classification Search
USPC .................. 601/148–152; 602/13, 23, 26, 27
See application file for complete search history.

(56) References Cited

U.S. PATENT DOCUMENTS

| | | | | |
|---|---|---|---|---|
| 5,169,384 | A | 12/1992 | Bosniak et al. | |
| 5,437,610 | A | 8/1995 | Cariapa et al. | |
| 5,466,250 | A | 11/1995 | Johnson, Jr. et al. | |
| 5,584,798 | A | 12/1996 | Fox | |
| 5,733,321 | A | 3/1998 | Brink | |
| 5,865,841 | A | 2/1999 | Kolen et al. | |
| 5,894,615 | A | 4/1999 | Alexander | |
| 5,925,010 | A | 7/1999 | Caprio, Jr. | |
| 5,989,285 | A | 11/1999 | DeVilbiss et al. | |
| 6,080,120 | A | 6/2000 | Sandman et al. | |
| 6,290,662 | B1 | 9/2001 | Morris et al. | |
| 6,352,550 | B1 | 3/2002 | Gildersleeve | |
| 6,440,093 | B1 | 8/2002 | McEwen et al. | |
| 6,530,941 | B1 | 3/2003 | Muller et al. | |
| 6,551,347 | B1 | 4/2003 | Elkins | |
| 6,610,084 | B1 | 8/2003 | Torres | |
| 6,736,787 | B1 | 5/2004 | McEwen et al. | |
| 7,198,093 | B1 | 4/2007 | Elkins | |
| 7,207,959 | B1 | 4/2007 | Chandran | |
| 7,211,104 | B2 | 5/2007 | Edelman | |
| 7,354,410 | B2 | 4/2008 | Perry et al. | |
| 7,396,345 | B2 | 7/2008 | Knighton et al. | |
| 7,442,175 | B2 | 10/2008 | Meyer et al. | |
| 2005/0143797 | A1 | 6/2005 | Parish et al. | |
| 2005/0187501 | A1* | 8/2005 | Ravikumar | 601/152 |
| 2007/0135743 | A1* | 6/2007 | Meyer | 601/152 |
| 2008/0058911 | A1 | 3/2008 | Parish et al. | |
| 2009/0069731 | A1 | 3/2009 | Parish et al. | |
| 2010/0210982 | A1 | 8/2010 | Balachandran et al. | |
| 2012/0209158 | A1* | 8/2012 | Avitable et al. | 601/151 |

* cited by examiner

*Primary Examiner* — Kristen Matter
(74) *Attorney, Agent, or Firm* — Rockey & Lyons; Matthew DePreter, Esq.

(57) ABSTRACT

A therapeutic compression device for applying compression force to a patient. The device is constructed of multiple layers, at least two of which are fluid-tight. At least two fluid-tight layers define a fluid-tight chamber that has a smaller surface area than the overall device. Fluid supplied to the fluid-tight chamber causes compressive force to be exerted on a patient. Preferably at least one layer is a fluid permeable material. An additional layer of fluid permeable material may be also be added to ensure a fluid permeable barrier exists between the fluid-tight chamber and a patient.

6 Claims, 7 Drawing Sheets

FIG. 4A
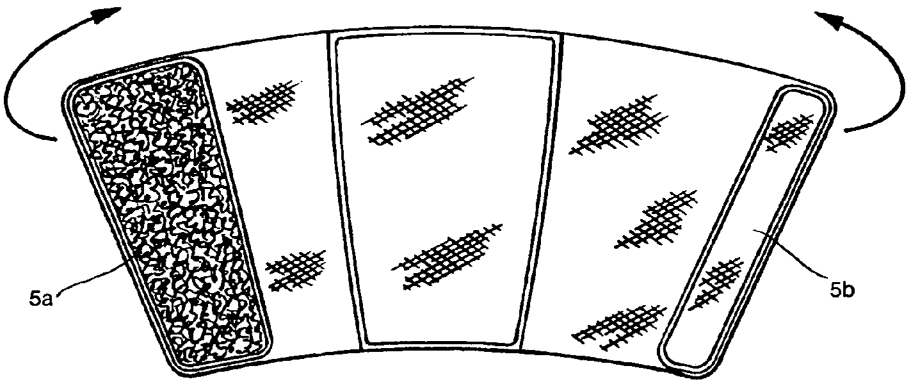
FIG. 4B
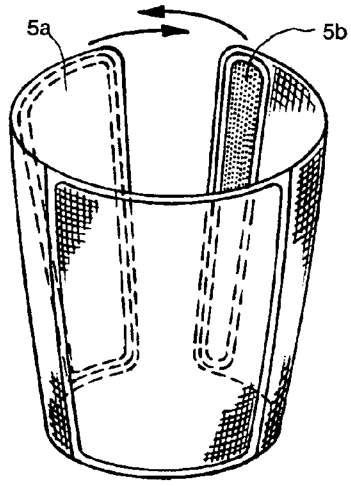
FIG. 4C
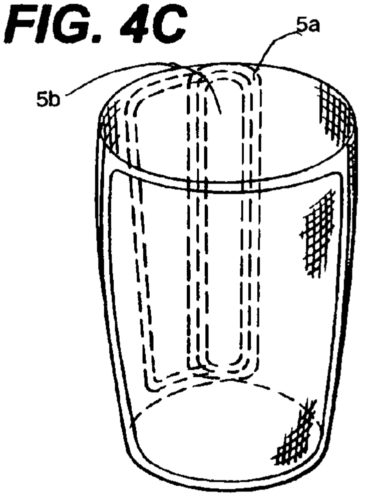
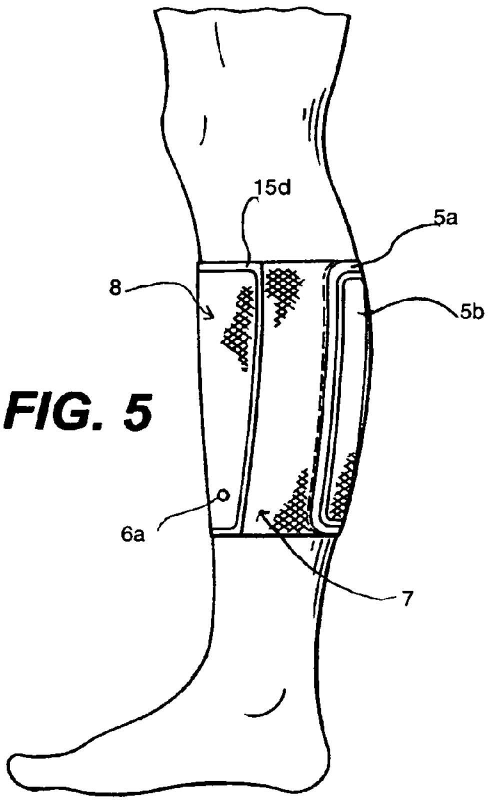
FIG. 5

THERAPEUTIC COMPRESSION APPARATUS

CROSS-REFERENCE TO RELATED APPLICATION

Not Applicable.

FEDERALLY SPONSORED RESEARCH OR DEVELOPMENT

Not Applicable.

BACKGROUND OF THE INVENTION

The present invention relates generally to compression systems used in the application of a compression force to a patient's body. More particularly, the invention is directed to a removable wrap that encompasses a portion of the patient's body, for example, a patient's leg. The wrap includes at least one fluid-tight chamber allowing for the ingress and egress of a fluid. The ingress of a fluid into the fluid-tight chamber causes the fluid-tight chamber to expand thereby applying a compression force to the patient's body in the location of the wrap.

Compression wraps similar to the invention described herein have been in use for many years. The wraps are designed to encompass an area of the patient's body where a compression force is desired. Once in place, a fluid (either a gas or a liquid) is forced into a fluid-tight chamber of the wrap thereby expanding the fluid-tight chamber. The wraps are constructed such that as the fluid-tight chamber expands, a compression force is applied to the portion of the patient's body encompassed by the wrap. Such wraps are often used in the treatment and prevention of deep vein thrombosis, but may have other uses as well.

As mentioned above, compression wraps similar to the present invention are constructed to encompass a portion of a patient's body, and include at least one fluid-tight chamber. Prior to the present invention, such wraps were constructed of two or more layers of fluid-tight material. The layers were of generally the same size and shape and were sealed together about the entirety of their perimeters in order to form a fluid-tight chamber between the layers. If more than two layers were used, more than one fluid-tight chamber would be formed. For example a three layer wrap, when sealed, would form two fluid-tight chambers.

The fluid-tight chamber, or fluid-tight chambers of such wraps could then be subdivided into smaller fluid-tight chambers, or could have one or more pathways formed within them. Examples of different wraps exhibiting the aforementioned construction are described in U.S. Pat. No. 7,211,104 issued to Edelman, U.S. Pat. No. 5,466,250 issued to Johnson, Jr. et al., U.S. Pat. No. 7,442,175 issued to Meyer et al., and U.S. Patent Application Publication 2008/0058911 filed on behalf of Parish et al.

Wraps of the aforementioned construction suffer from a number of shortcomings. For example, the material used to create the fluid-tight chambers is generally stiff (though not inflexible), and because that same material is used to create the entire wrap, the result is a wrap that is generally stiff and uncomfortable to wear. Additionally, because the material is fluid-tight, the material does not breathe, which can also be uncomfortable for the patient wearing the wrap. Another problem with the aforementioned wraps is that the fluid-tight material is expensive to manufacture. Because the foregoing wraps use the same fluid-tight material to form the entirety of the wrap, while also forming a fluid-tight chamber in only a portion of the wrap, that portion of the wrap that does not define the fluid-tight chamber needlessly utilizes two layers of expensive fluid-tight material where such material is neither needed nor desired.

As described in detail below, the present invention provides a unique solution to the aforementioned problems.

SUMMARY OF THE INVENTION

The present invention solves the aforementioned problems by utilizing an entirely different construction than the previously described wraps. According to the present invention, a single piece of material defines the shape of the desired wrap. Two layers of fluid-tight material are sealed together, preferably about their perimeter, thereby defining the desired shape of a fluid-tight chamber. The fluid-tight chamber is also equipped with a port for allowing the ingress and egress of fluid to the fluid-tight chamber. The fluid-tight chamber, which is of a smaller size that the size of the single piece of material, is integrated with the single piece of material by fusing the fluid-tight chamber and single piece of material together. For example, the single piece of material and the two layers of fluid-tight material may all be fused together using heat sealing or RF welding in a single step or in multiple steps. Thus the area defining the fluid-tight chamber is constructed using three layers of material, a first layer which is a portion of the single sheet of material, a second layer of fluid-tight material and a third layer of fluid-tight material.

By constructing the wrap as described above, cost of material can be decreased as the more expensive material used for defining the fluid-tight chamber is used only for that portion of the wrap where a fluid-tight chamber is necessary. The rest of the wrap, instead of using two pieces of the expensive fluid-tight material, is made only of the single sheet of material.

A further aspect of the present invention is utilizing a breathable material as the single sheet of material. Using a breathable material allows for air and moisture (such as sweat), that would otherwise be trapped between the patient wearing the wrap and the fluid-tight material of the wrap, to wick away from the patient. Using a breathable material thus helps prevent the buildup of heat and moisture against the patient making the wrap of the present invention more comfortable to wear. Also, it is desired that the single piece of material be more flexible than the fluid-tight material typically used. Utilizing a more flexible material makes the invention easier for the patient to apply and the wrap of the present invention more comfortable for the patient to wear.

Yet another aspect of the present invention is the addition of a fourth layer of material covering a portion of the area, but preferably the entire area, defined by the fluid-tight chamber. The fourth layer of material is a made of a breathable material and is fused to the wrap such that it covers at least a portion of the fluid-tight material on the side opposite the aforementioned single piece of material. Additionally, it is preferred that only part of the fourth layer be fused to the wrap. Fusing only part of the fourth layer to the wrap allows for an increase in airflow between the fourth layer and the fluid-tight chamber, making the wrap of the present invention more comfortable for the patient to wear.

It should be readily apparent that the order of the construction of the invention as described above is for explanation of the invention generally, and does not define the only method for constructing the invention. The present invention and its construction are described in more detail below.

BRIEF DESCRIPTION OF THE DRAWINGS

FIGS. 4A, 4B, and 4C are depictions of the operation of connectors utilized by an embodiment of the invention.

FIG. 5 is a depiction of an embodiment of the invention being worn by a patient.

DETAILED DESCRIPTION OF THE PREFERRED EMBODIMENT

In each of the drawings and throughout the specification, a number of the same components are repeatedly referred to. Thus, the same numerals are utilized to identify the same components throughout the specification. Additionally, simply because a component is not specifically shown or identified in a particular figure does not mean that the component is not included in an embodiment exhibiting the features actually depicted in the particular figure.

General Structure

Figure 1:
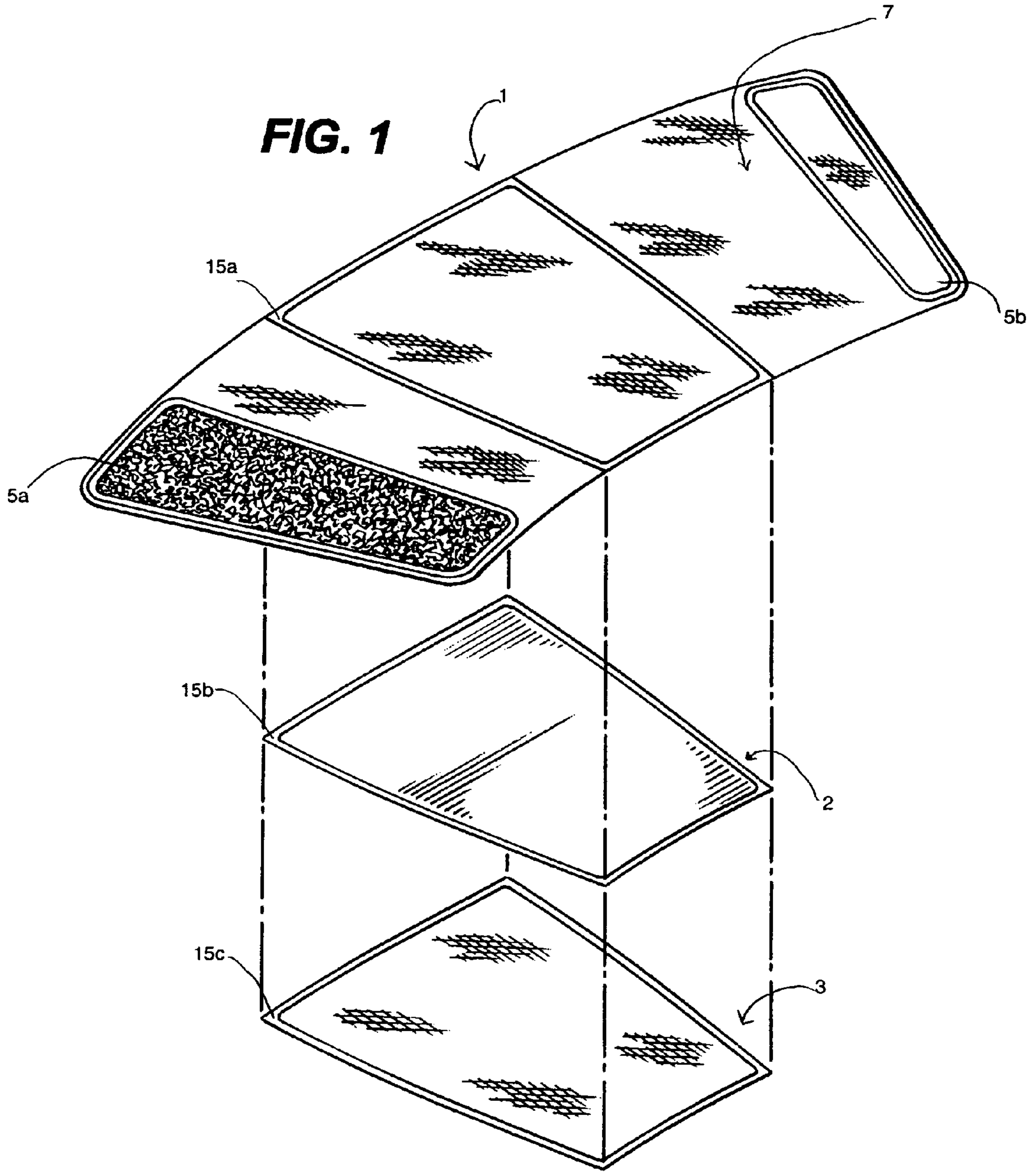
FIG. 1 is an exploded view of an embodiment of the invention.

FIG. 1 is an exploded view of the invention in the form of a leg or arm wrap. As shown, the wrap is comprised of a plurality layers. Although three layers are shown, it is contemplated that any number of layers, greater than two, could be used to form the present invention. In FIG. 1, first layer 1 defines the size and shape of the wrap while layers 2 and 3 define the size and shape of the fluid-tight chamber. Both layers 2 and 3 are of differing sizes and/or shapes than layer 1, and may be of differing sizes and/or shapes than each other. Ideally, however, layers 2 and 3 are of substantially the same size and shape.

As shown in the drawings, layer 1 is of a trapezoidal shape as such a shape best conforms to a patients arm or leg, but that is solely for explanatory purposes. It is contemplated that other shapes may be used such as a square, rectangle or oval. Indeed it is not necessary that the invention be formed in any one of those shapes, but instead could be formed in any shape or size.

All three layers are fused together. Preferably, the three layers are fused together such that a single weld about the perimeters of layers 2 and 3 creates a fluid-tight chamber between layers 2 and 3 and also fuses layers 2 and 3 to layer 1. As can bee seen in FIG. 1, the perimeter of the layer 2, identified by numeral 15*b*, and the perimeter of layer 3, identified by numeral 15*c*, are fused together and both layers are fused to layer 1 in the area identified by 15*a* where 15*a*, 15*b* and 15*c* are of the same length and width. Consequently, the weld along 15*a*, 15*b* and 15*c* forms a single integrated weld, identified as weld 15*d*, not shown in FIG. 1, and fuses layers 1, 2 and 3 together. Fusing the multiple layers together may be performed in one or more steps, though it is preferred that all of the layers are fused together in a single step. The wrap may also be provided with connectors 5*a* and 5*b*, described in further detail herein.

Figure 2:
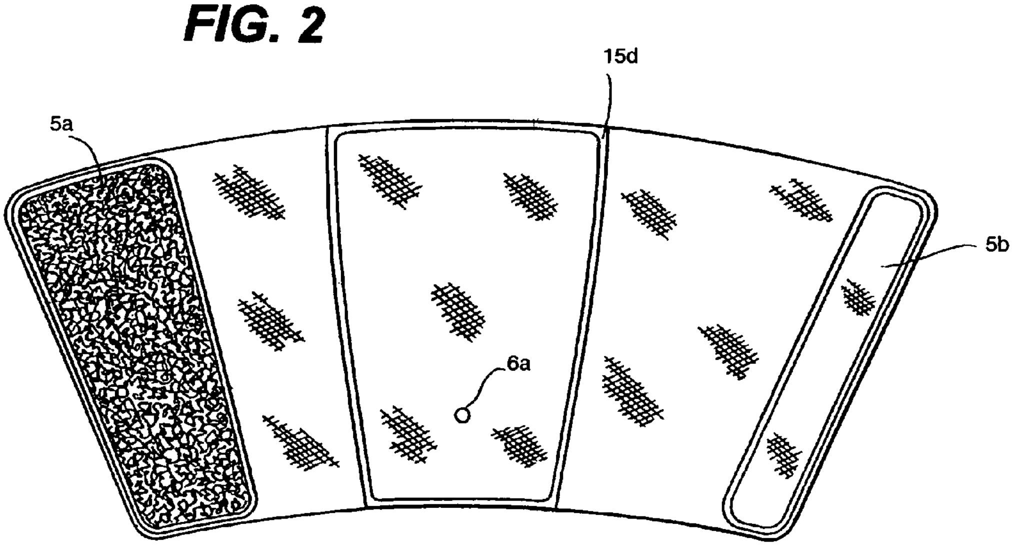
FIG. 2 is a plan view of an embodiment of the invention.
Figure 3:
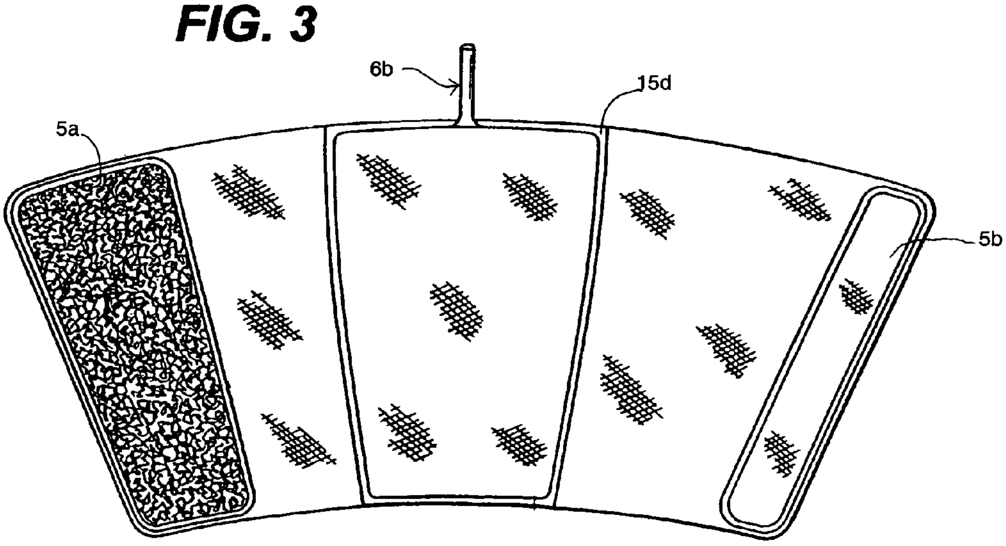
FIG. 3 is a plan view of an embodiment of the invention.

Additionally, at least one port is provided to allow for the ingress and egress of a fluid to the fluid-tight chamber defined by layers 2 and 3. FIG. 2 and FIG. 3 are plan views of the present invention. In FIG. 2, a port 6*a* is provided. Port 6*a* is a passage through layers 1 and 2 and provides for the ingress and egress of fluid to and from the fluid-tight chamber. An alternate embodiment is shown in FIG. 3 and utilizes a port 6*b* in the form of a tube. Port 6*b* may be provided between layers 2 and 3 such that it is integrated with weld 15*d*, 15*d* forming a fluid-tight seal between layers 2 and 3 and around port 6*b*. Additional ports may be utilized as well. In other embodiments, the use of multiple ports can allow for one port to be dedicated to the ingress of a fluid, while a differing port may be dedicated to the egress of a fluid. Other ports may be added to allow for the ingress and egress of differing fluids too.

As discussed above, the present invention may utilize one or more fluid-tight chambers. However, regardless of how many fluid-tight chambers are utilized, each fluid-tight chamber is equipped with at least one port.

The present invention may also be equipped with one or more connectors for joining parts of the invention together. In FIG. 4A, the present invention is laid flat and connectors 5*a* and 5*b* are identified. As shown in FIGS. 4B and 4C, the connectors 5*a* and 5*b*, which are themselves attached to the invention, wrap around and secure to one another. In the preferred embodiment, Velcro™ connectors are used, but any number of different connectors, such as snaps, buttons, clasps, etc. could be utilized.

Material Utilized by the Preferred Embodiment

As mentioned above, one drawback of previously constructed wraps is that they are constructed by fusing two layers of fluid-tight material together. That construction leads to wraps that tend to be relatively stiff. Additionally, those wraps do not allow for airflow between the wrap and the patient wearing the wrap because the layers of material forming the wrap are fluid-tight. Consequently, those wraps trap heat, air and moisture against the patient which may cause irritation and discomfort. Additionally, the fluid-tight material can be expensive, and using two layers of fluid-tight material to construct the entirety of the wrap, even portions of the wrap not adapted for the ingress and egress of a fluid, adds unwarranted cost to the construction of the wrap.

The structure of the preferred embodiment of the present invention alleviates those problems. Referring to FIG. 1, for example, layer 1 is made of a single piece of a material 7. Layers 2 and 3 are made of material having a different structure that material 7. Preferably, layers 2 and 3 are made of the same material, such as fluid-tight plastic, though it is contemplated that they may be made of differing materials, so long as the materials used are fluid-tight. Material 7, on the other hand, exhibits a different structure than the materials of layers 2 or 3, preferably a structure that is more flexible than the material of layers 2 or 3. Also, it is preferred that all three layers of material are polymer based or ester based, such that the layers may be fused together using heat sealing or RF welding.

Utilizing, as material 7, a material having a more flexible structure that that of layers 2 or 3, allows the invention to better conform to the particular shape of the patient as well as move and flex with the patient as the patient's body moves or alters shape. For example, where the invention is applied to a patient's calf, flexing of the calf muscles causes the shape of the patient's leg to change, and the flexible material 7 used by the present invention will move as well. However, because the fluid-tight materials of layers 2 and 3 are less flexible than the material 7, the fluid-tight chamber defined by layers 2 and 3 will be less likely than layer 1 to move when the patient's leg moves or changes shape. Thus, the compression applied to the patient's leg as a result of fluid being provided to the fluid-tight chamber will remain in the desired position relative to the patient, while the more flexible layer 1 adapts to the movement of the patient.

Instead of, or in addition to, being more flexible that the fluid-tight material of layers 2 and 3, it is preferable that material 7 is a fluid-permeable material. FIG. 5 is a depiction of a patient's leg wearing the present invention. The fluid-tight chamber 8 is positioned at the front of the patient's leg, while the connectors 5*a* and 5*b* are connected together at the back of the patient's leg securing the present invention in place. In FIG. 5, the fluid-tight chamber 8 is interposed between material 7 and the patient's leg in the area defined by seal 15*d* whereas other portions of the patient's leg are in direct contact with material 7. Utilizing a breathable material for material 7 allows for the circulation of air around at least a portion of the patient's leg. That airflow allows for moisture to be wicked away and/or heat to be dissipated from the patient in the area covered by material 7 alone. Thus the single layer of fluid-permeable material 7, by aiding in the removal of moisture and/or heat from the area of the patient covered by the invention, can provide the patient with a more comfortable experience while using the invention. Furthermore, utilizing only a single layer to form those portions of the invention where fluid-tight chambers need not be formed, as opposed to utilizing two layers of material to construct those portions, aids in reducing the cost of the invention as less material overall may be used.

Additional Aspects of the Preferred Embodiment

Figure 6:
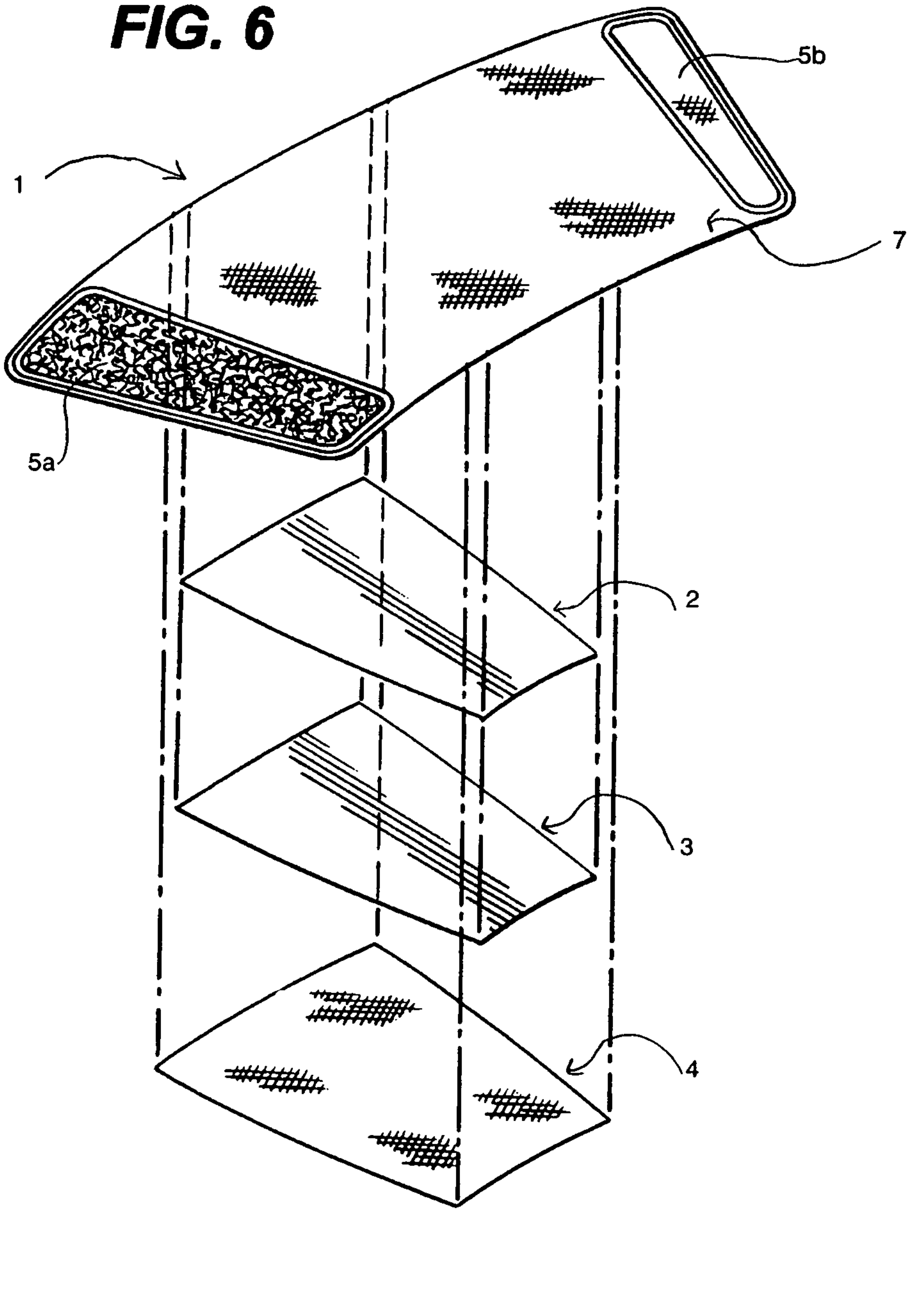
FIG. 6 is an exploded view of an embodiment of the invention.

The present invention may utilize an additional layer of fluid-permeable material as well. FIG. 6 is an exploded view of the present invention utilizing an additional layer of fluid-permeable material. As with the previously described embodiment, layers 2 and 3 are fused together forming a fluid-tight chamber between them. Layers 2 and 3 are also fused to layer 1 thereby integrating the fluid-tight chamber with layer 1. In a preferred embodiment, an additional layer of fluid-permeable material, layer 4, is also fused to layer 1.

It should be apparent that depending on the particular sizes and shapes of layers 1, 2, and 3, layer four may be fused to only layer 3, only layer 2, only layer 1 or some combination thereof. Also, additional layers may be interposed between layers 1 and 4, so long as layers 1 and 4, each made of a fluid-permeable material, remain the two outermost layers.

Preferably, layer 4 is larger than either layers 2 or 3 and therefore covers the entirety of the fluid-tight chamber defined by layers 2 and 3. Layer 4 may be fused to layer 1 in a variety of ways. However, it is preferred that only a portion of the perimeter of layer 4 is fused to layer 1. For example, in FIG. 7, connection points 9*a* and 9*b*, created using heat sealing or RF welding for example, correspond to the left and right sides of layer 4. However, the top and bottom of layer 4 are not connected to layer 1 or any other layer. Similarly, in FIG. 8, a plurality of connection points 9*c*, such as spot welds, fuse layer 4 and layer 1 together. By ensuring that a portion of the perimeter of layer 4 is not welded to layer 1 or any other layer, one or more air channels are formed between layer 4 and the layers of fluid-tight material.

When the invention utilizing layer 4 is applied to a patient, layer 4 is interposed between the patient and the layers of fluid-tight material. Thus, the patient is not in direct contact with the entirety of the fluid-tight material. Where layer 4 is larger than layers 2 and 3, the patient would not be in direct contact with any part of the fluid-tight layers. Layer 4 therefore creates a breathable layer between the patient and the fluid-tight layers.

Figure 7:
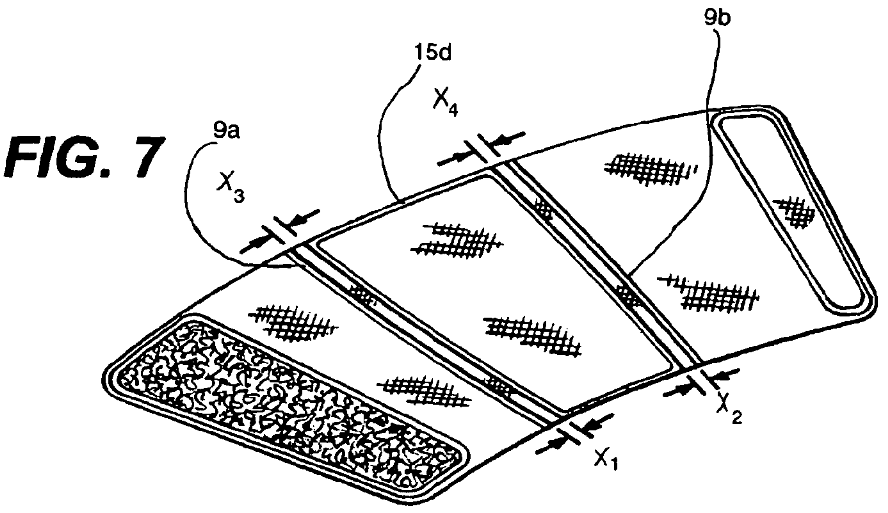
FIG. 7 is a plan view of the invention detailing particular connections between various layers of the invention.
Figure 8:
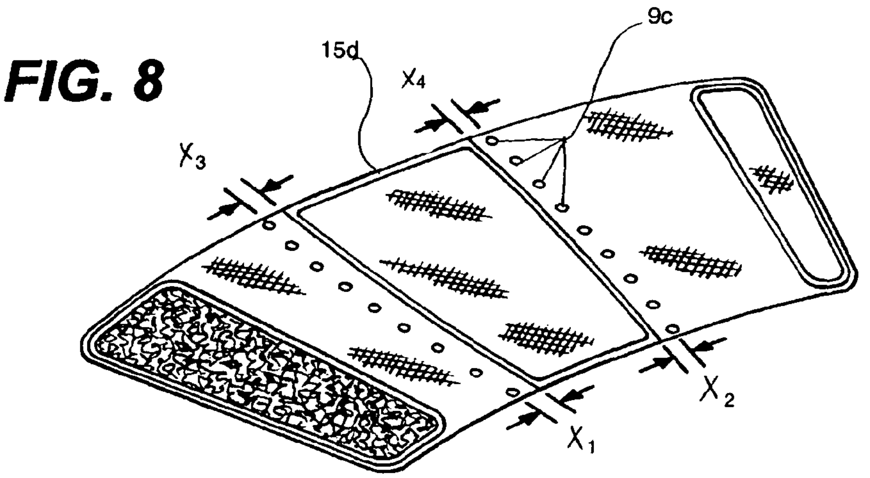
FIG. 8 is a plan view of the invention detailing particular connections between various layers of the invention.

As discussed above, it is preferred that layer 4 is fused to layer 1 such that only a portion of layer 4 is fused to layer 1. It is further preferred, as shown in FIGS. 7 and 8, that layer 4 be fused to layer 1 at some distance $x_1$, $x_2$, $x_3$ and $x_4$ away from weld 15*d*. The spaces $x_1$, $x_2$, $x_3$ and $x_4$ between welds 9*a*, 9*b* and 15*d* in FIG. 7 (or between spot welds 9*c* and weld 15*d* in FIG. 8) provide space for the fluid-tight chamber to expand and thus allow for the compressive force of the fluid-tight chamber to be applied to the patient rather than being restricted by layers 1 and 4. Additionally, while distances $x_1$, $x_2$, $x_3$ and $x_4$ need not be equal, it is preferred that they are substantially equal.

Additional Structure of the Fluid-Tight Chamber

Figure 9A:
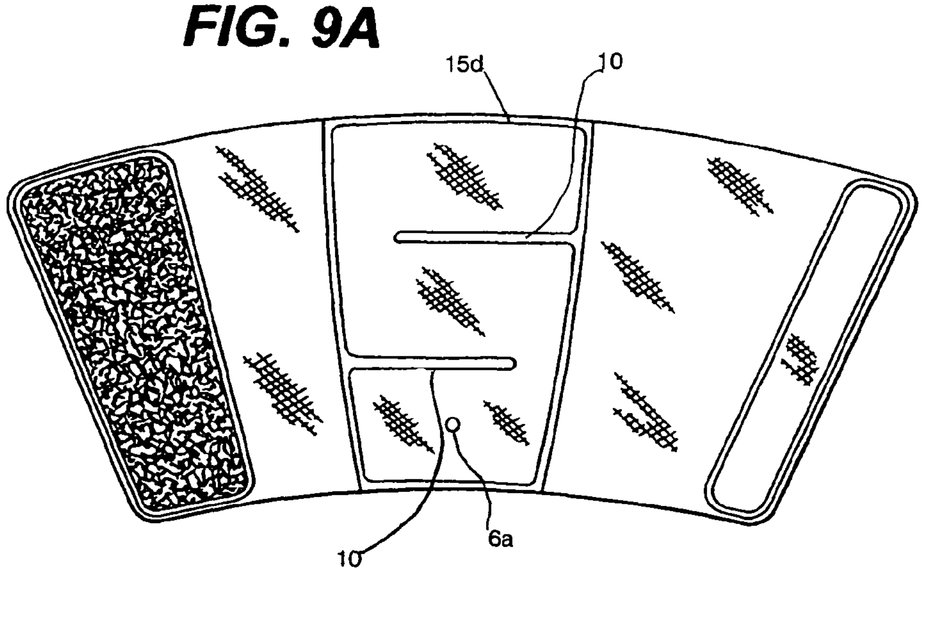
FIGS. 9A, 9B, 9C, 9D, and 9E are plan views of the invention further detailing the structure of the fluid-tight chamber of the invention.
Figure 9B:
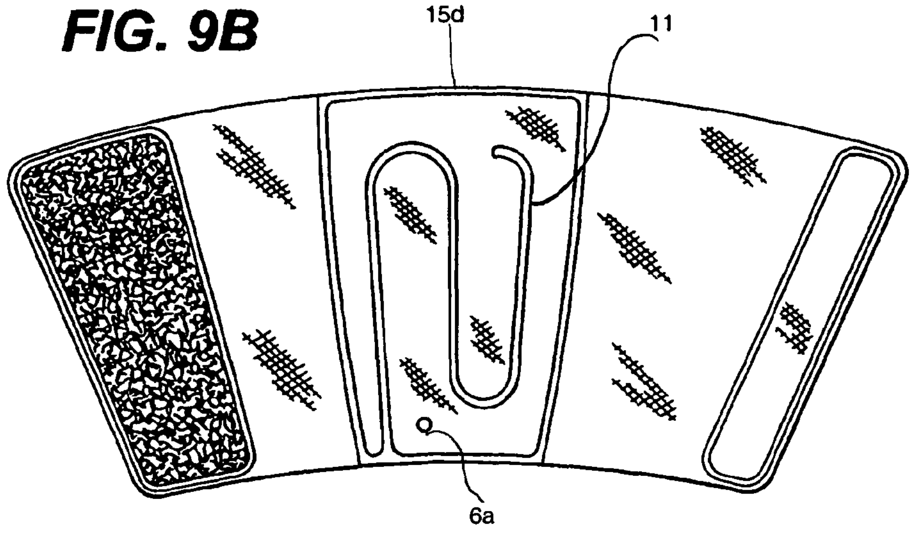
Figure 9C:
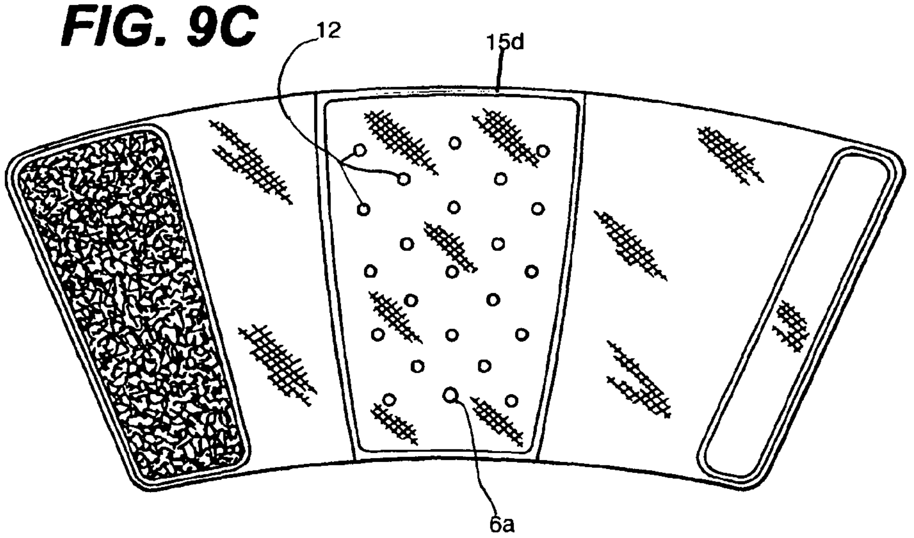
Figure 9D:
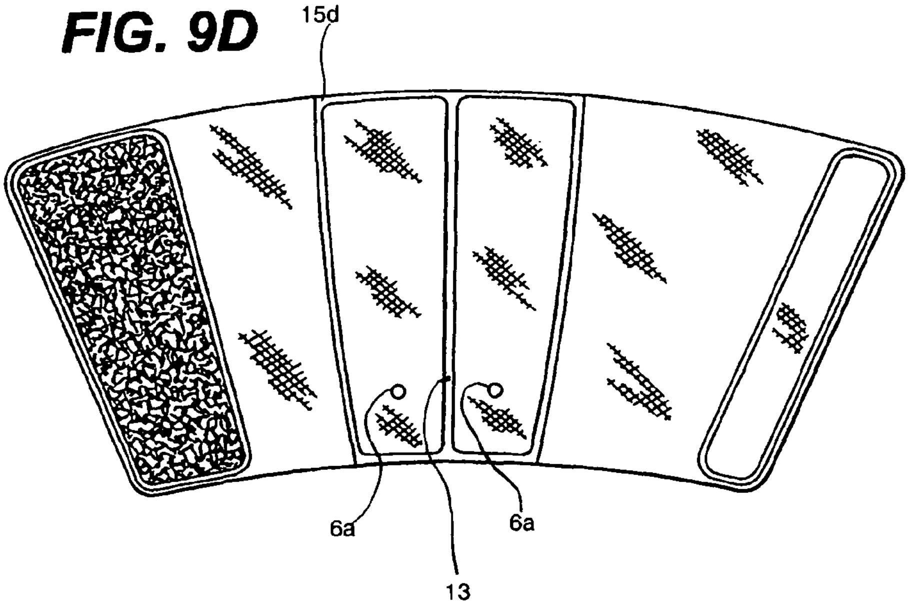
Figure 9E:
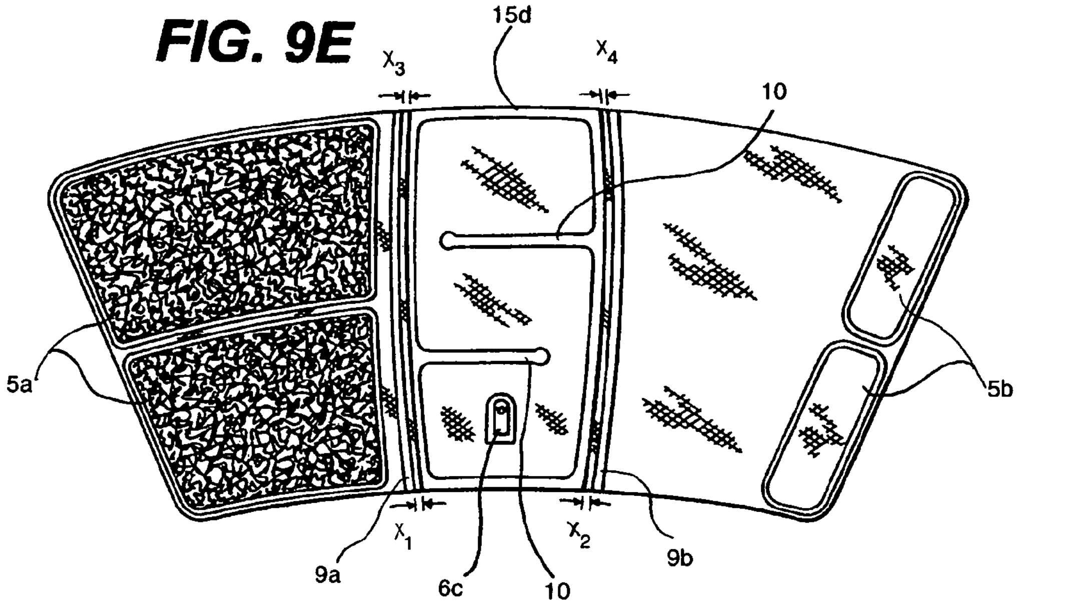

Once fused together, layers 2 and 3 form a fluid-tight chamber. However, it is recognized that a single large fluid-tight chamber will tend to fill unevenly when a fluid is supplied. Consequently, one or more additional connection points between at least layers 2 and 3 may be added in order to limit the expansion of the fluid-tight chamber when a fluid is supplied. For example, in FIG. 9A, additional connection points in the form of interjecting welds 10 are formed in the fluid-tight chamber. In FIG. 9B, an additional connection point in the form of a serpentine weld 11, which could be smooth or jagged, is formed in the fluid-tight chamber. In FIG. 9C, additional connection points in the form of a plurality of spot welds 12 are formed in the fluid-tight chamber. In FIG. 9D, the additional connection point 13 subdivides the fluid-tight chamber into two fluid-tight chambers. The presence of multiple fluid-tight chambers necessitates the use of at least two ports 6*a*, each port providing for the ingress and egress of fluid to their respective fluid-tight chamber. In FIG. 9E, an alternate embodiment is depicted. The Alternate embodiment of FIG. 9E utilizes multiple connectors 5*a* and 5*b*, weld 9*a* and 9*b* separated from weld 15*d* by spaces $x_1$, $x_2$, $x_3$ and $x_4$, interjecting welds 10 as well as a protruding port 6*c*.

Patient Use

Figure 10:
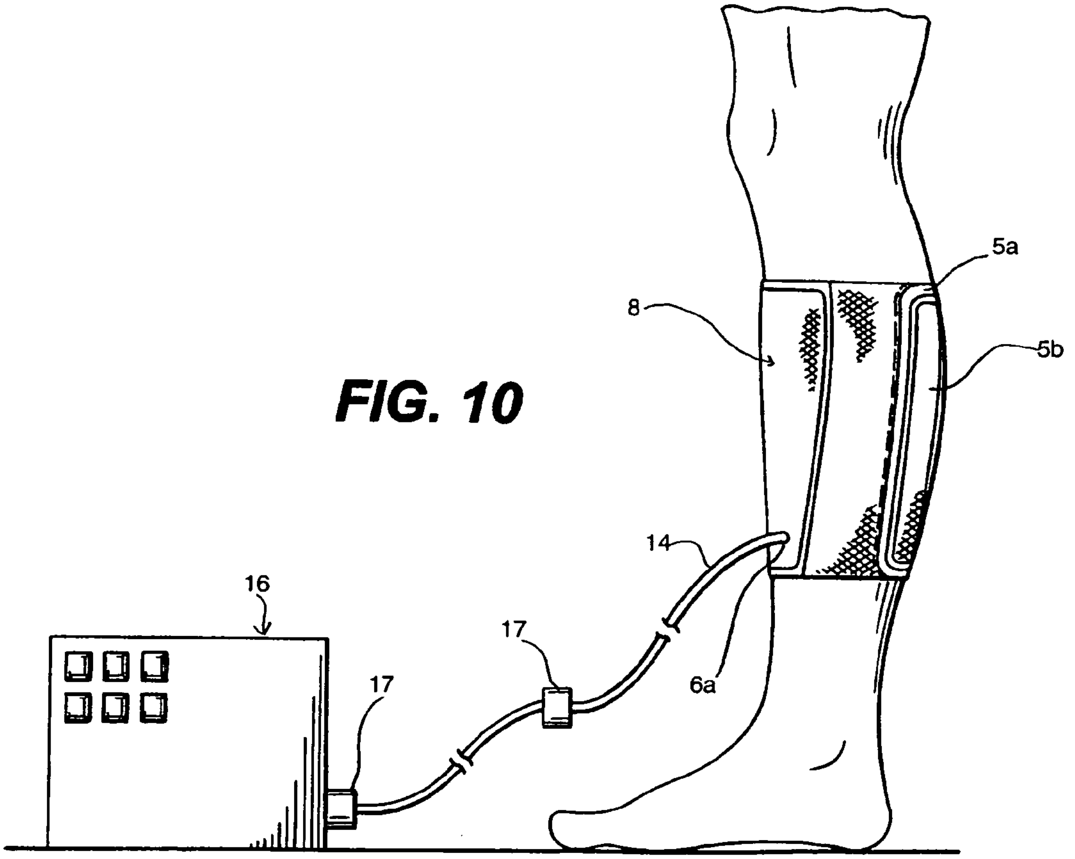
FIG. 10 is a depiction of the invention in use by a patient.

The present invention is particularly useful for applying a compression force to a localized area of a patient. To apply such compression force, the invention is applied to an area on the patient's body where the compression force is desired, a patient's leg for example, by wrapping the invention around the area. Utilizing the preferred embodiment, the connectors 5*a* and 5*b* of the invention are connected together to secure the invention in place. As shown in FIG. 10, a tube 14 is connected to port 6*a* using a fitment, quick connector, threaded connector or the like (not shown), although it is also contemplated that port 6*a* and tube 14 may be a single integrated piece. Tube 14 is further connected to a fluid supplying device 16, such as an air compressor of fluid pump using one or more fitments, quick connectors, threaded connectors or the like, identified in FIG. 10 by numeral 17. The fluid supplying device 16 may then be used to supply a fluid to the fluid-tight chamber 8 through tube 14 and port 6*a*. As fluid is supplied to the fluid-tight chamber 8, the fluid-tight chamber expands resulting in a compressive force being applied to the area of the patient where the invention is applied.

Although the present invention has been described in terms of the preferred embodiments, it is to be understood that such disclosure is not intended to be limiting. Various alterations and modifications will be readily apparent to those of skill in the art. Accordingly, it is intended that the appended claims be interpreted as covering all alterations and modifications as fall within the spirit and scope of the invention.

What is claimed is:

1. A therapeutic wrap comprising:

at least four layers, at least one of which is a larger layer having a surface area greater than the surface area than any other layer, wherein two of the layers are small layers of substantially the same size, each having a surface area that is less than the surface area of the larger layer, the small layers each being made of a fluid-tight material; wherein both of the small layers area fused to each other to create a trapezoidal fluid-tight chamber therebetween, and the fluid-tight chamber is also fused to the larger layer about the perimeter of the fluid-tight chamber;

a trapezoidal fourth layer having two equidistant sides, a top and a bottom and having a surface area less than the surface area of the larger layer and greater than the surface area of either smaller layer, the fourth layer being fused to the larger layer such that it covers the fluid-tight chamber, the material of both the fourth layer and the larger layer being fluid permeable; and wherein the fourth layer is fused to only the larger layer along each of the equidistant sides while the top and bottom of the fourth layer are not sealed to any of the larger layer or two small layers; and a port in fluid communication with the fluid-tight chamber.

2. A therapeutic wrap as in claim 1 further comprising:

at least one connector, said at least one connector being attached to the larger layer.

3. A therapeutic wrap as in claim 2 wherein at least one additional connection point is provided between said small layers, said at least one additional connection point fuses a portion of said small layers together to form at least one fluid pathway in said fluid-tight chamber.

4. A therapeutic wrap as in claim 1 wherein at least one additional connection point is provided between said small layers, said at least one additional connection point fuses a portion of said small layers together to form at least one fluid pathway in said fluid-tight chamber.

5. A therapeutic wrap as in claim 1 further comprising a hose extending from said port and at least one connector attached to a distal end of said hose.

6. A therapeutic wrap as in claim 5 wherein at least one additional connection point is provided between said small layers, said at least one additional connection point fuses a portion of said small layers together to form at least one fluid pathway in said fluid-tight chamber.

* * * * *